(12) United States Patent
Iyer

(10) Patent No.: US 8,644,002 B2
(45) Date of Patent: Feb. 4, 2014

(54) CAPACITOR INCLUDING REGISTRATION FEATURE FOR ALIGNING AN INSULATOR LAYER

(75) Inventor: Rajesh V. Iyer, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 13/149,600

(22) Filed: May 31, 2011

(65) Prior Publication Data

US 2012/0307416 A1 Dec. 6, 2012

(51) Int. Cl.
*H01G 4/35* (2006.01)
*H01G 7/00* (2006.01)

(52) U.S. Cl.
USPC .......................................... 361/502; 29/25.42

(58) Field of Classification Search
USPC .......................................... 361/302; 29/25.42
See application file for complete search history.

(56) References Cited

U.S. PATENT DOCUMENTS

| | | | |
|---|---|---|---|
| 3,920,888 A | 11/1975 | Barr | |
| 4,152,540 A | 5/1979 | Duncan et al. | |
| 4,420,652 A | 12/1983 | Ikeno | |
| 4,421,947 A | 12/1983 | Kyle | |
| 4,424,551 A | 1/1984 | Stevenson et al. | |
| 4,991,582 A | 2/1991 | Byers et al. | |
| 5,287,076 A | 2/1994 | Johnescu et al. | |
| 5,333,095 A | 7/1994 | Stevenson et al. | |
| 5,434,358 A | 7/1995 | Glahn et al. | |
| 5,470,345 A | 11/1995 | Hassler et al. | |
| 5,620,476 A | 4/1997 | Truex et al. | |
| 5,650,759 A | 7/1997 | Hittman et al. | |
| 5,683,435 A | 11/1997 | Truex et al. | |
| 5,685,632 A | 11/1997 | Schaller et al. | |
| 5,735,884 A | 4/1998 | Thompson et al. | |
| 5,750,926 A | 5/1998 | Schulman et al. | |
| 5,751,539 A | 5/1998 | Stevenson et al. | |
| 5,759,197 A | 6/1998 | Sawchuk et al. | |
| 5,782,891 A | 7/1998 | Hassler et al. | |
| 5,825,608 A | 10/1998 | Duva et al. | |
| 5,836,992 A | 11/1998 | Thompson et al. | |
| 5,866,851 A | 2/1999 | Taylor et al. | |
| 5,867,361 A | 2/1999 | Wolf et al. | |
| 5,870,272 A | 2/1999 | Seifried et al. | |
| 5,896,267 A | 4/1999 | Hittman et al. | |

(Continued)

FOREIGN PATENT DOCUMENTS

EP 1977786 A3 11/2011
JP 06120074 A * 4/1994

(Continued)

OTHER PUBLICATIONS

U.S. Appl. No. 13/596,944, by Rajesh V. Iyer, filed Aug. 28, 2012.

(Continued)

*Primary Examiner* — David M Sinclair

(57) ABSTRACT

In one example, a capacitor structure may include a capacitor comprising a surface that defines at least one feedthrough aperture and a ceramic insulator layer attached to the surface. The surface of the capacitor may include a capacitor registration feature, and the ceramic insulator layer may include a ceramic insulator layer registration feature. The capacitor registration feature and the ceramic insulator layer registration feature may cooperate to substantially align the ceramic insulator layer to the capacitor, e.g., prior to the ceramic layer being attached to surface of the capacitor.

8 Claims, 4 Drawing Sheets

(56) References Cited

U.S. PATENT DOCUMENTS

| | | | |
|---|---|---|---|
| 5,905,627 A | 5/1999 | Brendel et al. | |
| 5,959,829 A | 9/1999 | Stevenson et al. | |
| 5,973,906 A | 10/1999 | Stevenson et al. | |
| 5,999,398 A | 12/1999 | Makl et al. | |
| 6,008,980 A | 12/1999 | Stevenson et al. | |
| 6,275,369 B1 | 8/2001 | Stevenson et al. | |
| 6,414,835 B1 | 7/2002 | Wolf et al. | |
| 6,529,103 B1 * | 3/2003 | Brendel et al. | 333/182 |
| 6,566,978 B2 * | 5/2003 | Stevenson et al. | 333/182 |
| 6,660,116 B2 | 12/2003 | Wolf et al. | |
| 7,068,491 B1 | 6/2006 | Burdon et al. | |
| 7,196,899 B1 * | 3/2007 | Feger et al. | 361/512 |
| 7,668,597 B2 | 2/2010 | Engmark et al. | |
| 7,928,818 B2 | 4/2011 | Iyer | |
| 2002/0027484 A1 | 3/2002 | Stevenson et al. | |
| 2007/0060970 A1 | 3/2007 | Burdon et al. | |
| 2007/0203529 A1 | 8/2007 | Iyer et al. | |
| 2008/0195180 A1 | 8/2008 | Stevenson et al. | |
| 2009/0079517 A1 | 3/2009 | Iyer | |
| 2009/0079518 A1 | 3/2009 | Iyer | |
| 2009/0281603 A1 | 11/2009 | Lim | |
| 2010/0202096 A1 | 8/2010 | Iyer | |
| 2010/0284124 A1 | 11/2010 | Iyer | |
| 2011/0029036 A1 | 2/2011 | Yamamoto et al. | |
| 2011/0048770 A1 | 3/2011 | Reiterer et al. | |
| 2011/0102967 A1 | 5/2011 | Munns et al. | |

FOREIGN PATENT DOCUMENTS

| | | | |
|---|---|---|---|
| JP | 06244057 A | * | 9/1994 |
| WO | 9738752 A2 | | 10/1997 |
| WO | 2009117599 A2 | | 9/2009 |
| WO | 2010129731 A2 | | 11/2010 |
| WO | 2011014399 A1 | | 2/2011 |
| WO | 2011025667 A1 | | 3/2011 |

OTHER PUBLICATIONS

U.S. Appl. No. 13/308,136, by Rajesh V. Iyer, filed Nov. 30, 2011.
U.S. Appl. No. 13/308,222, by Rajesh V. Iyer, filed Nov. 30, 2011.
U.S. Appl. No. 13/346,424, by Rajesh V. Iyer, filed Jan. 9, 2012.
U.S. Appl. No. 13/308,271, by Rajesh V. Iyer, filed Nov. 30, 2011.
U.S. Appl. No. 13/308,144, by Rajesh V. Iyer, filed Nov. 30, 2011.
U.S. Appl. No. 13/308,313, by Rajesh V. Iyer, filed Nov. 30, 2011.
International Search Report and Written Opinion for international application No. PCT/US2012/039826, dated Nov. 23, 2012, 11 pages.
U.S. Appl. No. 13/196,661, by Kengo Morioka, filed Aug. 2, 2011.
U.S. Appl. No. 13/196,683, by Kengo Morioka, filed Aug. 2, 2011.
U.S. Appl. No. 13/196,695, by Kengo Morioka, filed Aug. 2, 2011.

* cited by examiner

CAPACITOR INCLUDING REGISTRATION FEATURE FOR ALIGNING AN INSULATOR LAYER

TECHNICAL FIELD

The disclosure relates to capacitors structures and, more specifically, capacitor structures used in an electrical feedthrough assembly.

BACKGROUND

An electrical feedthrough provides an electrical pathway between an interior of a hermetically-sealed housing of an electronics device to a point outside the housing. For example, an implantable medical device (IMD) may use one or more electrical feedthroughs to make electrical connections between electrical circuitry within the housing of the IMD and a lead, electrode, or sensor outside the housing. A feedthrough may comprise a ferrule that is mounted within an opening in the housing, a conductor that extends through the ferrule, and an insulating seal, which supports and electrically isolates the conductor from the ferrule.

Some IMDs include one feedthrough for each conductor exiting the IMD. As the electronics within the IMD are made smaller, the housing of the IMD may also be made smaller. In some implementations, the number of external leads, electrodes, or sensors that are coupled to an IMD has increased. In some cases, single-conductor feedthroughs are no longer used for some IMDs. Multi-conductor feedthroughs have been developed to provide hermetic pathways for a plurality of conductors (e.g., two or three or four or more) through the IMD housing. Some multi-conductor feedthroughs include a ceramic substrate mounted within a ferrule, and the ceramic substrate may include multiple conductive pathways formed in or through the ceramic substrate.

SUMMARY

In general, the disclosure is directed to a capacitor structure that includes a capacitor and a ceramic insulator layer attached to a surface of the capacitor. In some examples, the capacitor may be a monolithic discoidal capacitor, which includes a plurality of feedthrough apertures. The capacitor may include at least one capacitor registration feature, and the ceramic insulator layer may include at least one ceramic insulator layer registration feature. The at least one capacitor registration feature and the at least one ceramic insulator layer registration feature may cooperate to substantially align the ceramic insulator layer and the capacitor, e.g., when the capacitor and the ceramic insulator layer are in contact with each other. For example, the ceramic insulator layer may include a plurality of feedthrough apertures that correspond to the plurality of feedthrough apertures in the capacitor. The registration features of the capacitor and the ceramic insulator layer may facilitate alignment of the plurality of feedthrough apertures formed in the capacitor and the plurality of feedthrough apertures formed in the ceramic insulator layer. In some examples, after the capacitor and the ceramic insulator layer are aligned, the ceramic insulator layer may be laminated to a surface of the capacitor. In some examples, the ceramic insulator layer may reduce a likelihood or substantially prevent electrical arcing between an inner diameter of the capacitor and an outer diameter of the capacitor or between adjacent conductors received in adjacent apertures formed in the capacitor.

In one aspect, the disclosure is directed to a capacitor structure that includes a capacitor comprising a surface that defines at least one feedthrough aperture, and a ceramic insulator layer attached to the surface. According to this aspect of the disclosure, the surface comprises a capacitor registration feature, and the ceramic insulator layer includes a ceramic insulator layer registration feature. Additionally, the capacitor registration feature and the ceramic insulator layer registration feature cooperate to substantially align the ceramic insulator layer to the capacitor.

In another aspect, the disclosure is directed to a feedthrough assembly that includes a ferrule defining a ferrule aperture, a conductor, and a capacitor structure disposed within the ferrule aperture. According to this aspect of the disclosure, the capacitor structure includes a capacitor comprising a surface that defines a capacitor feedthrough aperture and a ceramic insulator layer attached to the surface. The surface comprises at least one capacitor registration feature, and the ceramic insulator layer includes a ceramic insulator layer registration feature and a ceramic insulator layer feedthrough aperture substantially aligned with the at least one capacitor feedthrough aperture. Further, the capacitor registration feature and the ceramic insulator layer registration feature cooperate to substantially align the ceramic insulator layer to the capacitor, and the conductor passes through the capacitor feedthrough aperture and the ceramic insulator layer feedthrough aperture.

In an additional aspect, the disclosure is directed to a method that includes substantially aligning at least one capacitor registration feature formed on a first surface of a capacitor with at least one ceramic insulator layer registration feature formed in a ceramic insulator layer. According to this aspect of the disclosure, the method also includes contacting the ceramic insulator layer to the first surface with the at least one capacitor registration feature and the at least one ceramic insulator layer registration feature in substantial alignment, and attaching the ceramic insulator layer to the first surface.

The details of one or more examples are set forth in the accompanying drawings and the description below. Other features, objects, and advantages will be apparent from the description and drawings, and from the claims.

DETAILED DESCRIPTION

Figure 1:
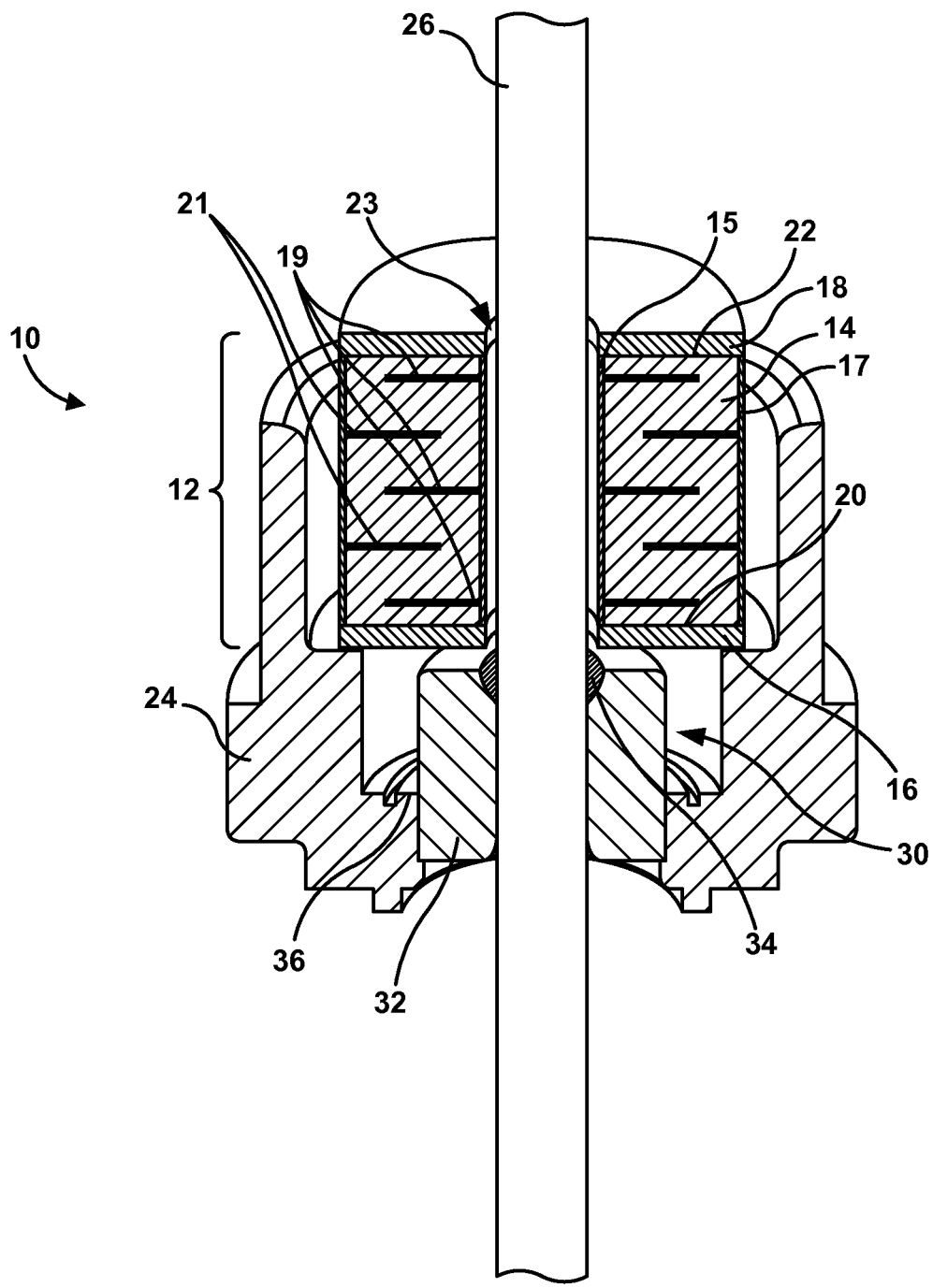
FIG. 1 is cross-sectional diagram of an example filtered feedthrough assembly that includes a discoidal capacitor and an attached ceramic insulative layer.

In general, the disclosure is directed to a capacitor structure that includes a capacitor and a ceramic insulator layer attached to a surface of the capacitor. In some examples, the capacitor may be a monolithic discoidal capacitor, which includes a plurality of feedthrough apertures. The capacitor may include at least one capacitor registration feature, and the ceramic insulator layer may include at least one ceramic insulator layer registration feature. The at least one capacitor registration feature and the at least one insulator layer registration feature may cooperate to align the ceramic insulator layer and the capacitor, e.g., when the ceramic insulator layer and the capacitor are in contact with each other. For example, the ceramic insulator layer may include a plurality of feedthrough apertures that correspond to the plurality of feedthrough apertures in the capacitor. The registration features of the capacitor and the ceramic insulator layer may cooperate to substantially align the plurality of feedthrough apertures formed in the capacitor and the plurality of feedthrough apertures formed in ceramic insulator layer. In some examples, once the capacitor and the ceramic insulator layer are substantially aligned, the ceramic insulator layer may be laminated to a surface of the capacitor.

In some cases, an IMD is implanted at a different location within the patient than the target tissue that is being stimulated and/or diagnosed. The IMD may be electrically coupled to a lead that includes electrical conductors that extend from the IMD to the electrodes or sensors located at the target tissue. At the IMD, the electrical conductors pass through a feedthrough or are electrically coupled to a conductive path through the feedthrough. The lead conductors may act as antennae that collect electromagnetic signals, including electromagnetic interference (EMI). The electromagnetic signals may be transmitted along the lead conductor, through the feedthrough, and to circuitry within the IMD. In some cases, the electromagnetic signals may interfere with normal IMD operations.

EMI due to stray electromagnetic signals conducted by the lead conductors may be addressed by incorporating a capacitor within the feedthrough assembly. The capacitor may act as a low-pass filter, transmitting relatively high frequency electromagnetic signals to ground (e.g., the housing of the IMD) and passing relatively low frequency signals to circuitry within the IMD. In some examples, the feedthrough assembly may include a multi-conductor feedthrough and a capacitor or capacitor array that accommodates multiple lead conductors. The capacitor or capacitor array may be attached to the multi-conductor feedthrough so that each of the conductive pathways through the multi-conductor feedthrough is electrically coupled to a corresponding conductive path in the capacitor or capacitor array while providing for a hermetic seal around each conductive pathway and between the multi-conductor feedthrough and the ferrule.

In other examples, an IMD may include one or more electrodes formed on a housing of the IMD (e.g., a leadless IMD). In some implementations, a leadless IMD may include a feedthrough assembly through which a conductor that connects the electrodes to circuitry within the leadless IMD passes. The capacitor structures and feedthrough assemblies described herein may also be utilized in leadless IMDs.

FIG. 1 is cross-sectional diagram of an example of a filtered feedthrough assembly 10 including a capacitor structure 12 in accordance with some aspects of this disclosure. In the example shown in FIG. 1, capacitor structure 12 includes a capacitor 14, a first ceramic insulator layer 16 attached to a first surface 20 of capacitor 14, and a second ceramic insulator layer 18 attached to a second surface 22 of capacitor 14. In the example illustrated in FIG. 1, capacitor 14 is a monolithic discoidal capacitor, such as one of the monolithic discoidal capacitors illustrated in FIGS. 2-6. However, examples other than that in which capacitor 14 is a monolithic discoidal capacitor are contemplated.

Although not illustrated in FIG. 1, capacitor 14 may include at least one capacitor registration feature, first ceramic insulator layer 16 may include at least one ceramic insulator registration feature, and second ceramic insulator layer 18 may include at least one ceramic insulator registration feature. Examples of capacitor registration features and ceramic insulator registration features will be described with reference to FIGS. 2-6. As will be described further below, such registration features may cooperate to align substantially align first and/or second ceramic insulator layer 16, 18 on a surface of capacitor 14.

FIG. 1 is one example of a filtered feedthrough assembly 10 in which capacitor structure 12 may be utilized. However, capacitor structure 12 may be used in other feedthrough assemblies, such as multipolar feedthrough assemblies that include a multipolar hermetically sealed feedthrough and a multipolar capacitor, such as a monolithic discoidal capacitor. Examples of other feedthrough assemblies in which capacitor structure 12 may be utilizes are described in copending and commonly assigned U.S. Patent Application Publication Number 2010/0284124, filed May 6, 2009, and entitled, "CAPACITOR ASSEMBLY AND ASSOCIATED METHOD," the entire contents of which are incorporated herein by reference.

As shown in FIG. 1, filtered feedthrough assembly 10 includes a ferrule 24 that defines an aperture through which conductor 26 (also referred to as a terminal pin or feedthrough pin) extends. Ferrule 24 is formed of a material that can be mounted within an aperture formed in the housing of an IMD. In some examples, the material from which ferrule 24 is formed may also be an electrically conductive material. Examples of materials from which ferrule 24 can be made include titanium, niobium, platinum, molybdenum, zirconium, tantalum, vanadium, tungsten, iridium, rhodium, rhenium, osmium, ruthenium, palladium, silver, and alloys, mixtures, and combinations thereof.

Joint-insulator sub-assembly 30 is disposed within the aperture defined by ferrule 24. Joint-insulator sub-assembly 30 secures conductor 26 relative to ferrule 24 and electrically insulates conductor 26 from ferrule 24. Joint-insulator sub-assembly 30 may also form a hermetic seal between conductor 26 and ferrule 24.

Joint-insulator sub-assembly 30 includes three components in the illustrated example: an insulator ring 32, a conductor-insulator braze 34, which may be made from gold, and an insulator-ferrule braze 36. Insulator ring 32 may be made from an electrically insulating material, such as an electrically insulating ceramic. Conductor-insulator braze 34 and insulator-ferrule braze 36 may include, for example, gold, platinum, a platinum alloy, or a nickel-gold alloy. In some examples, conductor-insulator braze 34 and insulator-ferrule braze 36 may include the same composition, while in other examples, conductor-insulator braze 34 may include a different composition than insulator-ferrule braze 36. When ferrule 24 is attached to the housing of an IMD, the lower portion of ferrule 24 (in the orientation shown in FIG. 1) and a portion of insulator ring 32 may be exposed to body fluids. Conductor-insulator braze 34 may form a hermetic seal between conductor 26 and insulator ring 32, and insulator-ferrule braze 36 may form a hermetic seal between insulator ring 32 and ferrule 24. The hermetic seal formed between ferrule 24, insulator ring 32, and conductor 26 may prevent ingress of body fluids into the interior of the housing of the IMD.

Conductor 26 provides a conductive path from circuitry within the housing of the IMD to one or more lead wires outside the housing of the IMD. As described above, these lead wires may act as antennae that collect EMI signals, which can interfere with operation of the circuitry within the IMD. Capacitor 14 may be disposed around conductor 26 such that conductor 26 passes through an aperture 23 formed in capacitor 14. In some examples, capacitor 14 may include a plurality of layers (not shown) of ceramic, such as barium titanate, with conductive active electrodes 19 and ground electrodes 21 formed on the layers, such as by printing the material of electrodes 19, 21, for example silver, silver-palladium, or silver-platinum, onto the layers before stacking and laminating the layers. In one example, active electrodes 19 electrically connect to a first conductive coating 15 formed on a circumference of aperture 23. First conductive coating 15 may be formed on at least a portion of the circumference of aperture 23 and, in some examples, may be formed on substantially the entire circumference of aperture 23. In some examples, first conductive coating 15 may extend substantially the entire height of capacitor 14, while in other examples, first conductive coating 15 may extend less than the entire height of capacitor 14. First conductive coating 15 may be formed of, for example, silver, silver-palladium, silver-platinum or another electrically conductive material. First conductive coating 15 may be electrically connected to conductor 26 using electrically conductive solder or epoxy.

Ground electrodes 21 are electrically connected to a common ground, as described in more detail below, such as via a second conductive coating 17. Similar to first conductive coating 15, second conductive coating may be formed of, for example, silver, silver-palladium, silver-platinum or another electrically conductive material. Second conductive coating 17 may be formed on at least a portion of the perimeter of capacitor 14 and, in some examples, may be formed on substantially the entire perimeter of capacitor 14. In some examples, second conductive coating 17 may extend substantially the entire height of capacitor 14, while in other examples, second conductive coating 17 may extend less than the entire height of capacitor 14. Although not shown in FIG. 1, second conductive coating 17 may be electrically connected to ferrule 24, e.g., using electrically conductive solder, epoxy, or a welding technique, such as laser welding.

When ferrule 24 is made of an electrically conductive material, a conductive pathway may exist between conductor 26 and the housing (not shown) of the IMD via capacitor 14 and ferrule 24. Capacitor 14 may be selected with electrical characteristics that result in relatively high frequency electrical signals, e.g., relatively high frequency EMI signals, being filtered by capacitor 14 and passed to the housing of the IMD via ferrule 24. The electrical characteristics of capacitor 14 may also be selected so capacitor 14 does not filter relatively low frequency electrical signals, e.g., signals representing sensed physiological parameters such as cardiac activity or neurological activity, and these relatively low frequency signals are passed by capacitor 14 and conducted by conductor 26 to circuitry within the housing of the IMD.

In some filtered feedthrough assemblies 10, capacitor structure 12 may include an electrically insulative coating on first surface 20 and/or second surface 22 that is formed of an epoxy or another electrically insulative polymer. However, as described above, in some examples, conductor 26 may be electrically connected to first conductive coating 15 using solder. Similarly, second conductive coating 17 may additionally or alternatively be connected to ferrule 24 using solder. Some solders, such as, e.g., lead-based solders, may have relatively low melting temperatures. In some implementations, lead-based solders are being substituted with lead-free solders, which may have a higher melting temperature than lead-based solders. In some examples, the solder (lead-free or lead-based) may have a eutectic point above a softening, melting, or degradation temperature of the epoxy or other electrically insulative polymer, which may make the epoxy or other electrically insulative polymers less desirable for use in capacitor structure 12.

First ceramic insulator layer 16 and second ceramic insulator layer 18 may be formed of an electrically insulating ceramic. In some examples, first ceramic insulator layer 16 and/or second ceramic insulator layer 18 include a low temperature cofired ceramic (LTCC) or a high temperature cofired ceramic (HTCC). First ceramic insulator layer 16 and/or second ceramic insulator layer 18 may be formed as a sheet or film that is cut to the desired shape and then laminated or otherwise attached to first surface 20 and/or second surface, respectively. LTCCs are ceramic materials with a sintering temperature less than about 1000° C. One example of an LTCC is a mixture of alumina and a glass. In some examples, the glass may include a calcia-alumina-silica-boron oxide glass. In an example, an LTCC may include a mixture of between about 90 wt. % and about 95 wt. % alumina and between about 5 wt. % and about 10 wt. % glass. HTCC are ceramic materials with a sintering temperature greater than about 1000° C. An example HTCC may include layers of alumina. Other electrically insulative ceramics may also be used in first ceramic insulator layer 16 and/or second ceramic insulator layer 18.

First ceramic insulator layer 16 and second ceramic insulator layer 18 may allow use of solders with higher eutectic temperatures (without affecting performance of layers 16, 18), which may facilitate replacement of lead-based solders with lead-free solders. As described above, in some examples, solders may be used to electrically connect conductor 26 to first conductive coating 15 and/or to electrically connect second conductive coating 17 to ferrule 24. In some examples, first ceramic insulator layer 16 and/or second ceramic insulator layer 18 are provided as films that are attached directly or indirectly to first surface 20 and second surface 22, respectively, of capacitor 14. For example, first ceramic insulator layer 16 and/or second ceramic insulator 18 may be adhered to first surface 20 and second surface 22 of capacitor 14 using an adhesive. In other examples, first ceramic insulator layer 16 and/or second ceramic insulator 18 may be laminated to first surface 20 and second surface 22 of capacitor 14 using heat and/or pressure.

In some examples, a surface of capacitor 14 (e.g., first surface 20 or second surface 22) may be electrically conductive. In other examples, first conductive coating 15 and/or second conductive coating 17 may extend to first surface 20 and/or second surface 22 of capacitor, and may provide conductive material at first surface 20 and/or second surface 22. The electrically conductive material at first surface 20 and/or second surface 22 may allow electrical arcing between conductor 26 and/or first conductive coating 15 and second conductive coating 17, or between adjacent conductors received in adjacent apertures formed in the capacitor (in a multipolar feedthrough, for example, FIGS. 2-6). For example, some electrical signals conducted by the one or more leads back to the IMD via conductor 26 may be relatively high voltage. For example, defibrillation shocks may have a voltage between about 780 V and about 800 V. Arcing at first surface 20 and/or second surface 22 may be more likely at higher voltages.

First ceramic insulator layer 16 and/or second ceramic insulator layer 18 may reduce or substantially prevent electrical arcing by providing electrical insulation at first surface 20 and/or second surface 22, respectively. The effectiveness of first ceramic insulator layer 16 and/or second ceramic insulator layer 18 in reducing the occurrence of arcing may be affected by how completely first ceramic insulator layer 16 and/or second ceramic insulator layer 18 cover conductive portions of first surface 20 and/or second surface 22, respectively. For example, first ceramic insulator layer 16 and/or second ceramic insulator layer 18 may be more effective in reducing the occurrence of arcing when first ceramic insulator layer 16 and/or second ceramic insulator layer 18 substantially fully cover portions of first conductive coating 15 and second conductive coating 17 that are otherwise exposed at first surface 20 and/or second surface 22. Because first ceramic insulator layer 16 and/or second ceramic insulator layer 18 may be provided as a film, the insulative film may be cut or otherwise shaped to substantially reproduce the features of first surface 20 and/or second surface 22, such as the perimeter of first surface 20 and/or second surface 22 and aperture 23 formed in first surface 20 and/or second surface 22. In some implementations, the insulative film may be cut or otherwise shaped prior to being laminated or otherwise attached to first surface 20 and/or second surface 22. In such implementations, relatively precise alignment between first surface 20 and first ceramic insulator layer 16 and/or between second surface 22 and second ceramic insulator layer 16 may improve coverage of first conductive coating 15 and second conductive coating 17 (or other conductive portions of first surface 20 and/or second surface 22), which may reduce or substantially prevent arcing. In accordance with one or more examples of the disclosure, capacitor registration features and ceramic insulator layer registration features may be employed to facilitate alignment of capacitor 14 and the ceramic insulator layer 16 and/or 18 when assembling capacitor structure 12.

Figure 2:
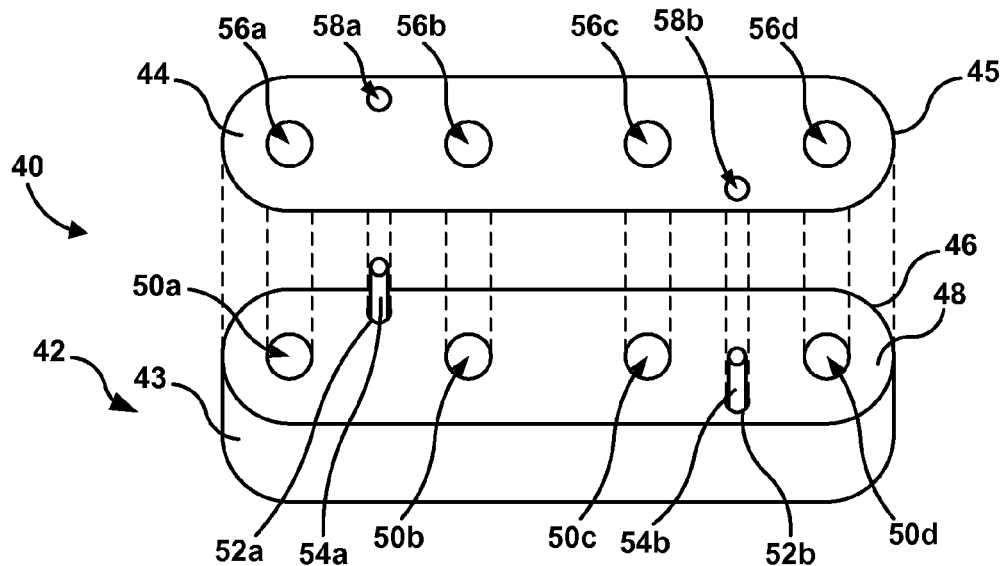
FIG. 2 is a perspective diagram of an example capacitor structure including a capacitor and a ceramic insulator layer prior to the ceramic insulator layer being attached to the capacitor.

FIG. 2 is a perspective diagram of an example capacitor structure 40 including a monolithic discoidal capacitor 42 and a ceramic insulator layer 44, prior to the ceramic insulator layer 44 being attached to the capacitor 42. Monolithic discoidal capacitor 42 may be substantially the same or similar to capacitor 14 described with reference to FIG. 1, e.g., may include multiple conductive active electrodes 19 and multiple conductive ground electrodes 21 formed on ceramic layers of monolithic discoidal capacitor 42. Monolithic discoidal capacitor 42 may also include conductive coatings substantially the same or similar to first conductive coating 15 on some or all of feedthrough apertures 50a, 50b, 50c, and 50d (collectively "feedthrough apertures 50") and a conductive coating substantially the same or similar to second conductive coating 15 on at least a portion of the perimeter sidewall 43 of capacitor 42. First conductive coating 15, second conductive coating 17, conductive active electrodes 19 and conductive ground electrodes 21 are not shown in FIG. 2 for purposes of clarity. Additionally, although FIGS. 2-6 illustrate a single ceramic insulator layer, in some examples, the capacitor structure may include a first ceramic insulator layer and a second ceramic insulator layer, such as capacitor structure 12 of FIG. 1. In examples in which the capacitor structure includes first and second ceramic insulator layers, one or both of the insulator layers and one or both of the surfaces to which the insulator layers attach may include registrations features as described herein.

Monolithic discoidal capacitor 42 includes a first surface 48 that defines a capacitor perimeter 46. Perimeter sidewall 43 joins first surface 48 along capacitor perimeter 46. First surface 48 defines four feedthrough apertures 50, which extend substantially through monolithic discoidal capacitor 42 to a second surface (not shown) opposite first surface 48 (similar to aperture 23 illustrated in FIG. 1). Feedthrough apertures 50 are configured to receive a conductor or termination pin (e.g., conductor 26 of FIG. 1). Although monolithic discoidal capacitor 42 includes four feedthrough apertures 50 in FIG. 1, monolithic discoidal capacitor 42 may include other numbers of feedthrough apertures 50, such as at least one, at least two, at least three, or the like.

First surface 48 further defines a first capacitor registration aperture 52a and a second capacitor registration aperture 52b (collectively "capacitor registration apertures 54"). Capacitor registration apertures 52 are registration features that facilitate alignment of ceramic insulator layer 44 to first surface 48 of monolithic discoidal capacitor 42. Capacitor registration apertures 52 may be cavities that extend at least partially through monolithic discoidal capacitor 42. In some examples, capacitor registration apertures 52 extend only partially through monolithic discoidal capacitor 42, while in other examples, capacitor registration apertures 52 extend fully through monolithic discoidal capacitor 42 from first surface 48 to the second surface (not shown) opposite first surface 48. In some examples, monolithic discoidal capacitor 42 may include one registration aperture or may include more than two registration apertures. In general, monolithic discoidal capacitor 42 may include at least one registration aperture. In some examples in which monolithic discoidal capacitor 42 includes a single registration aperture, the registration aperture (and corresponding registration pin and registration aperture in ceramic insulator layer 44) may include a non-circular shape, such as an ellipse, a rectangle, a square, a cross, or another polygonal shape, which may facilitate alignment of monolithic discoidal capacitor 42 and ceramic insulator layer 44, e.g., by promoting both linear and rotational alignment of capacitor 42 and layer 44. Additionally or alternatively, registration apertures 52 may be located at different positions of first surface 48 than the positions illustrated in FIG. 2.

As shown, first registration pin 54a may be inserted in first capacitor registration aperture 52a, and second registration pin 54b may be inserted in second capacitor registration aperture 52b. First registration pin 54a and second registration pin 54b (collectively "registration pins 54") may be formed of a material that does not melt, soften, or fuse to monolithic discoidal capacitor 42 and/or ceramic insulator layer 44 during lamination of ceramic insulator layer 44 to first surface 48. For example, registration pins 54 may be formed of a high melting metal such as tantalum, niobium, a tantalum alloy, or a niobium alloy, or ceramic material, such as alumina, that sinters at a higher temperature than the temperature at which ceramic insulator layer 44 is laminated to first surface 48.

Capacitor registration apertures 52 and registration pins 54 are formed to have complementary shapes and sizes. For example, capacitor registration apertures 52 may be circular and registration pins 54 may be cylindrical, with a circular cross-section, as shown in FIG. 2. In other examples, capacitor registration apertures 52 may have another shape, such as an ellipse, a rectangle, a square, or another polygonal shape, and registration pins 54 may have a corresponding cross-sectional shape. Additionally, the size (e.g., diameter, circumference, or perimeter) of registration pins 54 may be selected to that the perimeter surfaces of registration pins 54 closely engage with or contact the perimeter of capacitor registration apertures 52. A close fit between registration pins 54 and capacitor registration apertures 52 may facilitate alignment of ceramic insulator layer 44 to first surface 48. Registration pins 54 may be sufficiently long to extend through ceramic insulator layer 44 when ceramic insulator layer 44 is placed in contact with first surface 48.

Ceramic insulator layer 44 defines a perimeter 45 and four feedthrough apertures 56a, 56b, 56c, and 56d (collectively "feedthrough apertures 56"). Additionally, ceramic insulator layer 44 defines a first ceramic insulator registration aperture 58a and a second ceramic insulator registration aperture 58b (collectively "registration apertures 58"). The number, sizes, and positions of feedthrough apertures 56 and registration apertures 58 are merely examples, and other examples of ceramic insulator layer 44 may include different numbers, sizes, and/or positions of feedthrough apertures 56 and registration apertures 58. In general, ceramic insulator layer 44 may include the same number of feedthrough apertures 56 as the number of feedthrough apertures 50 formed in monolithic discoidal capacitor 42.

The relative positions of registration apertures 58, feedthrough apertures 56, and perimeter 45 are such that when registration apertures 58 are aligned to capacitor registration apertures 52, feedthrough apertures 56 substantially align with feedthrough apertures 50 and perimeter 45 substantially aligns with perimeter 46. In this way, registration apertures 58, capacitor registration apertures 52 and registration pins 54 cooperate to substantially align ceramic insulator layer 44 to first surface 48 of monolithic discoidal capacitor 42.

Registration apertures 58 of ceramic insulator layer 44 may be substantially similar in size and shape as capacitor registration apertures 52. For example, registration apertures 58 may be circular, elliptical, rectangular, square, or another polygonal shape. As described with respect to capacitor registration apertures 52, a close fit between registration pins 56 and registration apertures 58 may facilitate alignment of ceramic insulator layer 44 to first surface 48.

To assemble capacitor structure 40, monolithic discoidal capacitor 42 may be formed with feedthrough apertures 50 and registration apertures 52, either during initial manufacture of capacitor 42, or during a subsequent machining step. Various techniques may be used to form feedthrough apertures 50 and registration apertures 52, such as drilling, laser cutting, water jet cutting, or the like. In some examples, first conductive coating 15 may be formed on at least a portion of at least some of feedthrough apertures 50, and second conductive coating 17 may be formed on at least a portion of perimeter sidewall 43.

Ceramic insulator layer 44 may be formed from a ceramic insulator film, such as a LTCC film or a HTCC film. In some examples, ceramic insulator layer 44 may be cut from the film using, for example, laser cutting. During the formation of ceramic insulator layer 44, feedthrough apertures 56 and registration apertures 58 may be formed in ceramic insulator layer 44 using, for example, the same process used to cut ceramic insulator layer 44. The cutting process may be controlled by a computer, such as a computer numerical control (CNC) machine, to facilitate precise relative positioning of perimeter 45, feedthrough apertures 56, and registration apertures 58.

Registration pins 54 are then placed in capacitor registration apertures 52 and ceramic insulator layer 44 is positioned on first surface 48, with registration apertures 58 aligned to registration pins 54. Registration apertures 58, registration pins 54, and registration apertures 52 cooperate to substantially align ceramic insulator layer 44 and first surface 48 of monolithic discoidal capacitor 42. For example, ceramic insulator layer 44, including feedthrough apertures 56 and perimeter 45 may be substantially aligned to first surface 48 of monolithic discoidal capacitor 42, including feedthrough apertures 50 and perimeter 46.

Once registered, ceramic insulator layer 44 may be attached to first surface 48. In some implementations, ceramic insulator layer 44 may be adhered to first surface 48 using an adhesive, such as a polyimide material, a glass material, or the like. In other examples, ceramic insulator layer 44 may be laminated to first surface 48 using temperature and pressure. For example, when ceramic insulator layer 44 includes a LTCC, layer 44 may be laminated to first surface 48 at a temperature of between about 800° C. and about 900° C. and a pressure of between about 800 pounds per square inch (psi) and about 1500 psi. After ceramic insulator layer 44 is laminated to first surface 48, registration pins 54 may be removed.

Figure 3:
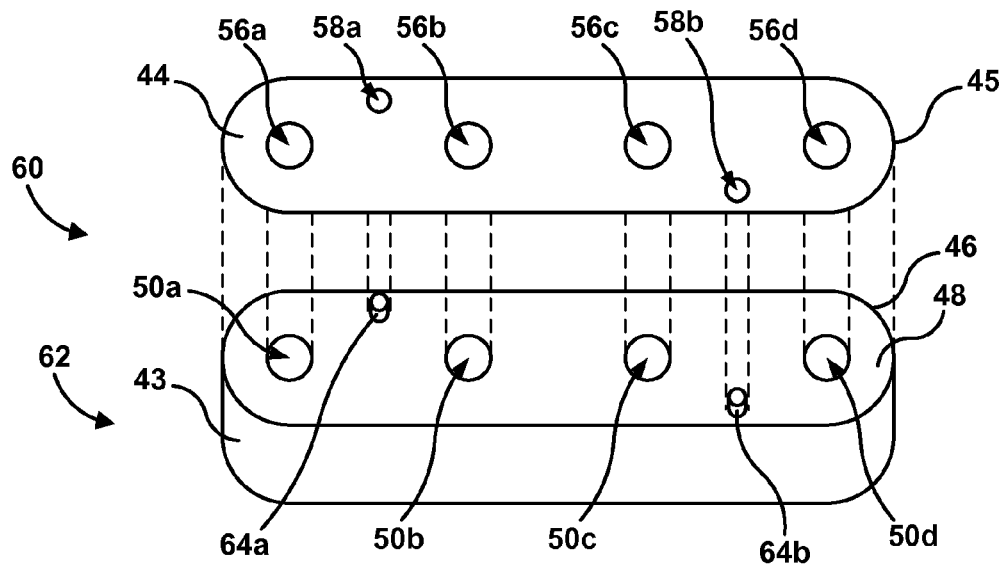
FIG. 3 is a perspective diagram of another example capacitor structure including a capacitor and a ceramic insulator layer prior to the ceramic insulator layer being attached to the capacitor.

FIG. 3 is a perspective diagram of an example capacitor structure 60 that includes a monolithic discoidal capacitor 62 and a ceramic insulator layer 44, prior to the ceramic insulator layer 44 being attached to the capacitor 62. As described with reference to FIG. 2, ceramic insulator layer 44 defines a perimeter 45, feedthrough apertures 56 and registration apertures 58.

Monolithic discoidal capacitor 62 includes a first surface 48 that defines a perimeter 46, which joins perimeter sidewall 43, as described with respect to FIG. 2. Additionally, first surface 48 defines four feedthrough apertures 50. Instead of including registration apertures 52 defined by first surface 48, as described with respect to monolithic discoidal capacitor 42 in FIG. 1, monolithic discoidal capacitor 62 includes a first registration protrusion 64a and a second registration protrusion 64b (collectively "registration protrusions 64") formed on first surface 48. Registration protrusions 64 are capacitor registration features that facilitate alignment of first surface 48 and ceramic insulator layer 44. In some examples, monolithic discoidal capacitor 62 may include one registration protrusion or may include more than two registration protrusions. In general, monolithic discoidal capacitor 62 may include at least one registration protrusion. As described above with respect to FIG. 2, in some examples, a single registration protrusion may include a non-circular shape, such as an ellipse, square, rectangle, cross, or other polygon. Additionally or alternatively, registration protrusions 62 may be located at different positions of first surface 48 than the positions illustrated in FIG. 3.

In some examples, registration protrusions 64 are formed of one of the materials from which monolithic discoidal capacitor 62 is formed. For example, registration protrusions 64 may be formed of an electrically insulating ceramic material used in monolithic discoidal capacitor 62, such as barium titanate. In some examples, registration protrusions 64 may be formed during the manufacture of monolithic discoidal capacitor 62. In other examples, registration protrusions 64 may be formed separately from the manufacture of monolithic discoidal capacitor 62, e.g., prior to attaching ceramic insulator layer 44 to first surface 48.

Registration protrusions 64 and registration apertures 58 are formed to have complementary shapes and sizes. For example, registration protrusions 64 may be cylindrical, with a circular cross-section, and registration apertures 58 may be circular, as shown in FIG. 3. In other examples, registration protrusions 64 may have another cross-sectional shape, such as an ellipse, a rectangle, a square, or another polygonal shape, and registration apertures 58 may have a corresponding shape. Additionally, the size (e.g., diameter, circumference, or perimeter) of registration protrusions 64 may be selected to that the perimeter surfaces of registration apertures 58 closely engage with or contact the perimeter of registration protrusions 64. A close fit between registration protrusions 64 and registration apertures 58 may facilitate alignment of ceramic insulator layer 44 to first surface 48. Registration protrusions 64 may be sufficiently long to extend through ceramic insulator layer 44 when ceramic insulator layer 44 is placed in contact with first surface 48.

The relative positions of registration apertures 58, feedthrough apertures 56, and perimeter 45 are such that when registration apertures 58 are mated with registration protrusions 64, feedthrough apertures 56 substantially align with feedthrough apertures 50 and perimeter 45 substantially aligns with perimeter 46. In this way, registration apertures 58 and registration protrusions 64 cooperate to substantially align ceramic insulator layer 44 to first surface 48 of monolithic discoidal capacitor 62.

Figure 4:
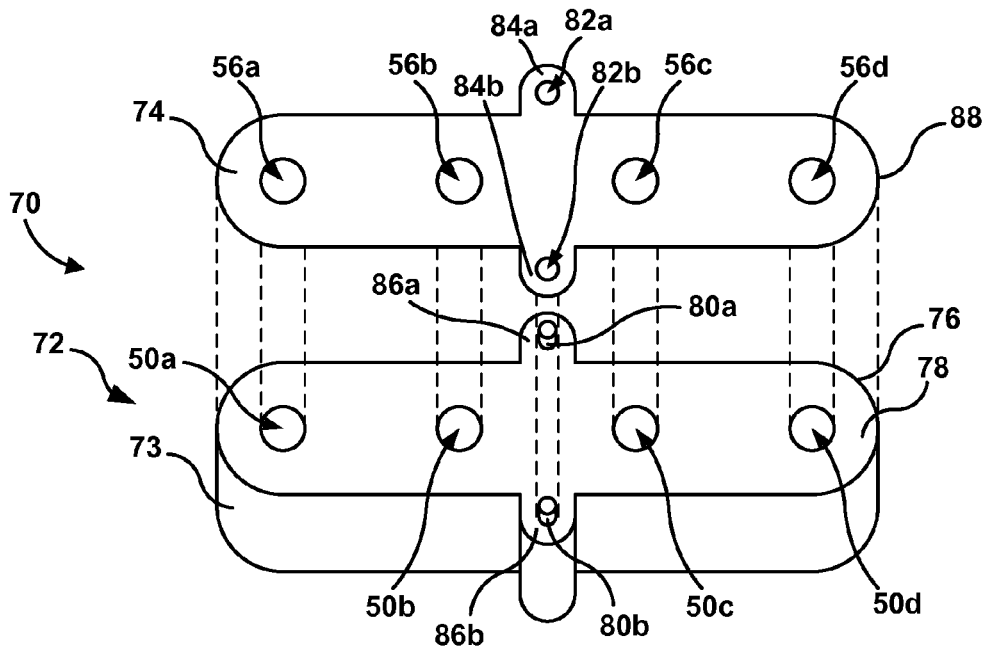
FIG. 4 is a perspective diagram of another example capacitor structure including a capacitor and a ceramic insulator layer prior to the ceramic insulator layer being attached to the capacitor.

FIG. 4 is a perspective diagram of an example capacitor structure 70 including a monolithic discoidal capacitor 72 and a ceramic insulator layer 74, prior to the ceramic insulator layer 74 being attached to the capacitor 72.

Monolithic discoidal capacitor 72 includes a first surface 78 that defines four feedthrough apertures 50. As described above, in other examples, first surface 78 may define another number of feedthrough apertures 50, and generally may define at least one feedthrough aperture. Additionally, first surface 78 defines a perimeter 76, which joins perimeter sidewall 73. In FIGS. 2 and 3, monolithic discoidal capacitors 42, 62 defined a substantially discoidal (e.g., oval or elliptical) perimeter. In the example shown in FIG. 4, monolithic discoidal capacitor 72 defines a perimeter 76 that includes a first projection 86a and a second projection 86b (collectively "projections 86") that disrupt the discoidal shape of capacitor 72. Projections 86 are part of perimeter sidewall 73 and may extend from first surface 78 to a second surface (not shown) opposite first surface 78.

On the portions of first surface 78 that are part of projections 86, a first registration protrusion 80a and a second registration protrusion 80b (collectively "registration protrusions 80") are formed. Registration protrusions 80 are similar to registration protrusions 64 described with reference to FIG. 3. Registration protrusions 80 are capacitor registration features that facilitate alignment of first surface 78 and ceramic insulator layer 74.

Although FIG. 4 illustrates a monolithic discoidal capacitor 72 that includes two projections 86 and two registration protrusions 80, in other examples, monolithic discoidal capacitor 72 may include more than two projections 86 and/or more than two registration protrusions 80. In some examples, each one of projections 86 includes a registration protrusions 80 formed thereon. Additionally or alternatively, one or more registration protrusion 80 may be formed on a portion of first surface 78 that is not part of one of projections 86.

In some examples, projections 86 and/or registration protrusions 80 are formed of one of the materials from which monolithic discoidal capacitor 72 is formed. For example, projections 86 and/or registration protrusions 80 may be formed of an electrically insulating ceramic material used in monolithic discoidal capacitor 72, such as barium titanate. In some examples, projections 86 and/or registration protrusions 80 may be formed during the manufacture of monolithic discoidal capacitor 72. In other examples, projections 86 and/or registration protrusions 80 may be formed separately from the manufacture of monolithic discoidal capacitor 72, e.g., prior to attaching ceramic insulator layer 74 to first surface 78.

Ceramic insulator layer 74 defines a perimeter 88 and four feedthrough apertures 56. Ceramic insulator layer 74 includes a first projection 84a and a second projection 84a (collectively "projections 84"), which substantially match in size and align with projections 86 of monolithic discoidal capacitor 72. Ceramic insulator layer 74 defines a first ceramic insulator registration aperture 82a in first projection 84a and a second ceramic insulator registration aperture 82b in second projection 84b. In general, ceramic insulator layer 74 may include the same number and positioning of feedthrough apertures 56, projections 84, and capacitor registration apertures 82 as the number and positioning of feedthrough apertures 50, projections 86, and registration protrusions 80 formed in monolithic discoidal capacitor 72. Similar to registration protrusions 64 and registration apertures 58 of FIG. 3, registration protrusions 80 and registration apertures 82 are formed to have complementary shapes and sizes. The relative positions of projections 84, registration apertures 82, feedthrough apertures 56, and perimeter 88 are such that when registration apertures 82 are aligned to registration protrusions 80, feedthrough apertures 56 substantially align with feedthrough apertures 50 and perimeter 88 substantially aligns with perimeter 76. In this way, registration apertures 82 and registration protrusions 80 cooperate to substantially align ceramic insulator layer 74 to first surface 78 of monolithic discoidal capacitor 72.

Figure 5:
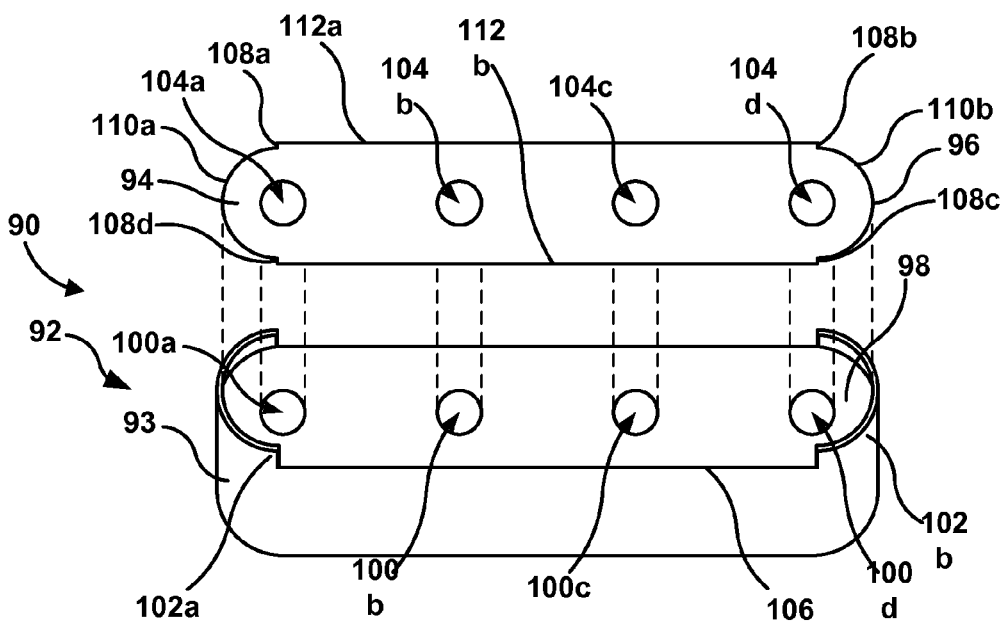
FIG. 5 is a perspective diagram of another example capacitor structure including a capacitor and a ceramic insulator layer prior to the ceramic insulator layer being attached to the capacitor.

FIG. 5 is a perspective diagram of an example capacitor structure 90 including a monolithic discoidal capacitor 92 and a ceramic insulator layer 94, prior to the ceramic insulator layer 94 being attached to the capacitor 92. In the example illustrated in FIG. 5, the capacitor registration features include a first registration protrusion 102a and a second registration protrusion 102b (collectively "registration protrusions 102") that extend substantially normal from first surface 98 of monolithic discoidal capacitor 92 along at least a portion of the perimeter 106 of monolithic discoidal capacitor 92. The ceramic insulator registration features include the perimeter 96 of ceramic insulator layer 94.

Monolithic discoidal capacitor 92 includes a first surface 98 that defines four feedthrough apertures 100a, 100b, 100c, 100d (collectively "feedthrough apertures 100"). As described above, in other examples, first surface 98 may define another number of feedthrough apertures 100, and generally defines at least one feedthrough aperture. Additionally, first surface 98 defines a perimeter 106, which joins perimeter sidewall 93. Perimeter sidewall 93 extends from first surface 98 to a second surface (not shown) substantially opposite first surface 98. In the example shown in FIG. 5, monolithic discoidal capacitor 92 defines registration protrusions 102 that extend substantially normal (perpendicular) from first surface 98. In FIG. 5, registration protrusions 102 run along the curved portions of perimeter 106 of first surface 98. In other examples, monolithic discoidal capacitor 92 may include more than two registration protrusions 102, and at least one of registration protrusions 102 may be located at a different position along perimeter 106. In some examples, monolithic discoidal capacitor 92 may include a single protrusion that is formed along at least a portion of perimeter 106. In some implementations, the single protrusion may be formed along substantially the entire length of perimeter 106. In general, monolithic discoidal capacitor 92 may include at least one projection formed along perimeter 106. Registration protrusions 102 may have a height, measured from first surface 98, that is at least as great as a thickness of ceramic insulator layer 94.

Ceramic insulator layer 94 defines a perimeter 96, a first feedthrough aperture 104a, a second feedthrough aperture 104b, a third feedthrough aperture 104c, and a fourth feedthrough aperture 104d (collectively "feedthrough apertures 104"). In general, ceramic insulator layer 94 includes the same number and positioning of feedthrough apertures 104 as the number and positioning of feedthrough apertures 100 formed in monolithic discoidal capacitor 92.

Perimeter 96 of ceramic insulator layer 94 is formed and sized so ceramic insulator layer 94 substantially covers first surface 98 and perimeter 96 substantially aligns with registration protrusions 102. For example, as illustrated in FIG. 5, perimeter 96 includes a first stepped portion 108a, a second stepped portion 108b, a third stepped portion 108c, and a fourth stepped portion 108d (collectively "stepped portions 108"). Perimeter 96 also includes a first curved portion 110a, a second curved portion 110b (collectively "curved portions 110"), a first straight portion 112a, and second straight portion 112b (collectively "straight portions 112"). First stepped portion 108a connects first curved portion 110a and first straight portion 112a. Second stepped portion 108b connects first straight portion 112a and second curved portion 110b. Third stepped portion 108c connects second curved portion 110b and second straight portion 112b. Fourth stepped portion 108c connects second straight portion 112b and first curved portion 110a.

Stepped portions 108, curved portions 110, and straight portions 112 are sized and shaped so that ceramic insulator layer 94 covers substantially all of first surface 98 and stepped portions 108 and curved portions 110 contact registration protrusions 102 to substantially align ceramic insulator 94 and first surface 98. For example, stepped portions 108 and curved portions 110 may contact registration protrusions 102 to substantially align feedthrough apertures 100 of monolithic discoidal capacitor 92 and feedthrough apertures 104 of ceramic insulator layer 104. In this way, perimeter 96 and registration protrusions 102 cooperate to substantially align ceramic insulator layer 94 to first surface 98 of monolithic discoidal capacitor 92.

Figure 6:
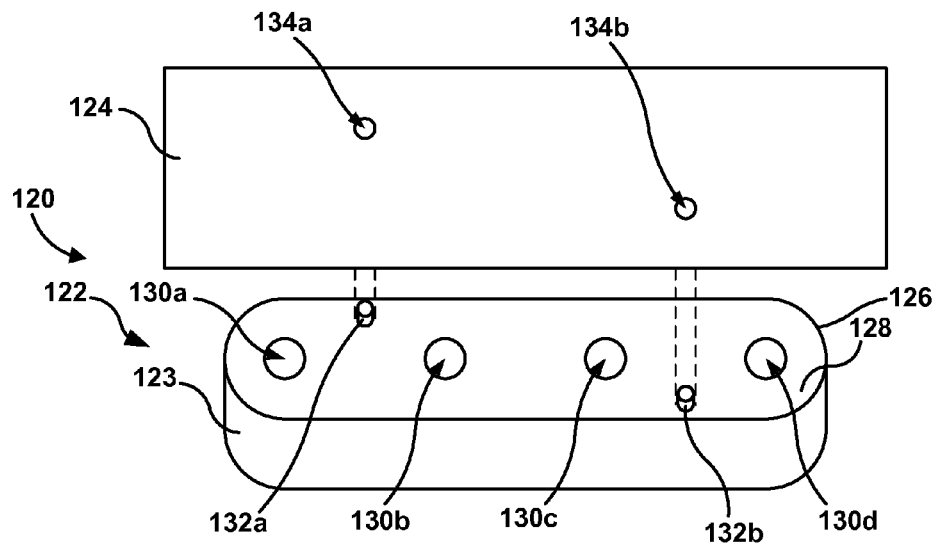
FIG. 6 is a perspective diagram of another example capacitor structure including a capacitor and a ceramic insulator layer prior to the ceramic insulator layer being attached to the capacitor.

Although the examples shown in FIGS. 2-5 illustrate ceramic insulator layers in which feedthrough apertures and perimeters are defined prior to aligning the ceramic insulator layer with the monolithic discoidal capacitor, in some examples, the ceramic insulator layer and the monolithic discoidal capacitor may be aligned before forming the perimeter and/or feedthrough apertures in the ceramic insulator layer. FIG. 6 is a perspective diagram of an example capacitor structure 120 including a monolithic discoidal capacitor 122 and a ceramic insulator layer 124, prior to the ceramic insulator layer 124 being attached to the capacitor 122, and prior to the perimeter and feedthrough apertures being defined in ceramic insulator layer 124.

In the example illustrated in FIG. 6, monolithic discoidal capacitor 122 includes a first surface 128 that defines a perimeter 126, which joins perimeter sidewall 123. Additionally, first surface 128 defines four feedthrough apertures 130a, 130b, 130c, 130d (collectively "feedthrough apertures 130"). Monolithic discoidal capacitor 122 includes a first registration protrusion 132a and a second registration protrusion 132b (collectively "registration protrusions 132") formed on first surface 128. Registration protrusions 132 may be the same or substantially similar to registration protrusions 64 described with respect to FIG. 3 and/or registration protrusions 80 described with respect to FIG. 4.

Ceramic insulator layer 124 includes a film that defines a first registration aperture 134a and second registration aperture 134b (collectively "registration apertures 134"). Registration protrusions 132 and registration apertures 134 are formed to have complementary numbers, shapes, and sizes, as described above.

After registration apertures 134 are aligned with registration protrusions 132, ceramic insulator layer 124 is placed in contact with first surface 128. Registration apertures 134 and registration protrusions 132 cooperate to substantially align ceramic insulator layer 124 to first surface 128 of monolithic discoidal capacitor 122. Once in contact with first surface 128, ceramic insulator layer 124 may be adhered or laminated to first surface 128, as described above. After ceramic insulator layer 124 is laminated to first surface 128, feedthrough apertures may be cut in ceramic insulator layer 124 at positions substantially corresponding to feedthrough apertures 130 of monolithic discoidal capacitor 122. Additionally, ceramic insulator layer 124 may be cut to define a perimeter that substantially corresponds to perimeter 126 of monolithic discoidal capacitor 122. In some examples, ceramic insulator layer 124 may be cut using laser cutting.

Alternatively, ceramic insulator layer 124 may be cut after placing layer 124 in contact with first surface 128 and before adhering or laminating layer 124 to first surface 128. Once the perimeter of ceramic insulator layer 124 and the feedthrough apertures of ceramic insulator layer 124 have been cut, ceramic insulator layer 124 may be adhered, laminated or otherwise attached to first surface 128.

Although FIGS. 2-6 primarily described registration apertures formed in the ceramic insulator layer and registration pins or registration protrusions extending from the capacitor, in other examples, a registration depression or aperture may be formed in the surface of the capacitor and registration protrusions may be formed on the ceramic insulator layer. In some examples, the ceramic insulator layer may include both a registration aperture and a registration protrusion, and the capacitor may include corresponding registration protrusion and registration depression or aperture. Additionally or alternatively, although FIGS. 2-6 have been described as separate examples, the registration features described in each figure may be used in combination with each other. For example, a capacitor may include a protrusion that extends from the surface of the capacitor along a perimeter of the capacitor (FIG. 6) and may also include a protrusion formed away from the perimeter of the capacitor (e.g., FIG. 3).

Figure 7:
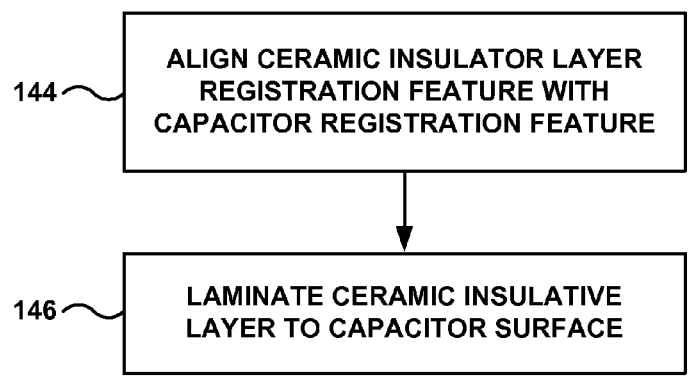
FIG. 7 is a flow diagram that illustrates an example technique that can be used to form an example capacitor structure.

FIG. 7 is a flow diagram that illustrates an example technique that can be used to form a capacitor structure in accordance with some examples of the disclosure. The example technique of FIG. 7 will be described primarily with respect to capacitor structure 40 (FIG. 2); however, the technique may be applicable to capacitor structure 60 of FIG. 3, capacitor structure 70 of FIG. 4, capacitor structure 90 of FIG. 5, capacitor structure 120 of FIG. 6, or other capacitor structures. In general, the technique may include aligning at least one ceramic insulator layer registration feature with at least one capacitor registration feature (e.g., capacitor registration apertures 52 and registration pins 54) (144). As described above, the at least one ceramic insulator layer registration feature may include a registration aperture (e.g., registration apertures 58, 82, 134), a perimeter of the ceramic insulator layer (e.g., perimeter 96), and/or a feature formed in the perimeter of the ceramic insulator layer (e.g., stepped portions 108 and curved portions 110). The at least one capacitor registration feature may include, for example, capacitor registration apertures 52 and registration pins 54 or registration protrusions 64, 80, 102, 132. The capacitor registration features and the ceramic insulator layer registration features cooperate to substantially align the ceramic insulator layer to the surface of the monolithic discoidal capacitor.

Once at least one ceramic insulator layer registration feature with at least one capacitor registration feature are aligned (144), ceramic insulator layer 44 may be placed in contact with first surface 48 of monolithic discoidal capacitor 42 and be attached to first surface 48 (146). As described above, ceramic insulator layer 44 may be adhered or laminated to first surface 48. For example, when ceramic insulator layer 44 includes a LTCC, layer 44 may be laminated to first surface 48 at a temperature of between about 800° C. and about 900° C. and a pressure of between about 800 pounds psi and about 1500 psi.

In some examples, feedthrough apertures 56 and perimeter 45 of ceramic insulator layer 42 may be formed prior to laminating ceramic insulator layer 44 to monolithic discoidal capacitor 42 (146). In other examples, feedthrough apertures 56 and perimeter 45 of ceramic insulator layer 42 may be formed after laminating ceramic insulator layer 44 to monolithic discoidal capacitor 42 (146), as described above.

EXAMPLE

A ceramic insulator that includes an LTCC composition was laminated onto a surface of a monolithic discoidal capacitor to form a capacitor structure. The LTCC composition including between about 90 wt. % about 95 wt. % alumina and between about 5 wt. % and about 10 wt. % glass ($CaO$—$Al_2O_3$—$SiO_2$—$B_2O_3$). The LTCC composition was laminated to the capacitor at between about 800° C. and about 900° C. at a pressure of between about 800 psi and about 1500 psi.

The capacitor structure was then assembled in a feedthrough assembly. The capacitor structure was connected to the feedthrough pins in the feedthrough apertures and the feedthrough ferrule along the capacitor perimeter using solder. The capacitor was connected to ground via electrical connection to the ferrule.

The feedthrough assembly was subjected to thermal shock testing of 5 cycles between −55° C. and 125° C. and burn-in at about 125° C. and a 1000V bias voltage applied between the feedthrough pins and the ferrule.

After burn-in conditioning, the feedthrough assembly was electrically tested. First, the feedthrough assembly was subjected to a pulse test with 1300V between the feedthrough pins and the ground, and 1000V between adjacent feedthrough pins. The rise time of the pulse was between about 1 and 2 microseconds and the dwell time of the pulse was about 18 milliseconds.

The feedthrough assembly also was subjected to a dielectric withstand voltage test. A voltage of 1300V was applied between the feedthrough pins and the ground, and 1000V was applied between adjacent feedthrough pins. Each of the voltages was held for about 5 seconds at peak voltage.

Finally, the feedthrough assembly was subjected to an insulation resistance test. A voltage of 1300V was applied between the feedthrough pins and the ground, and 1000V was applied between adjacent feedthrough pins. The resistance was measured, and was greater than 30 gigaohms. The feedthrough assembly and capacitor structure passed all the above tests with no failures.

Various examples have been described. These and other examples are within the scope of the following claims.

The invention claimed is:

1. A method comprising:
substantially aligning at least one capacitor registration feature formed on a first surface of a capacitor with at least one ceramic insulator layer registration feature formed in a ceramic insulator layer;
contacting the ceramic insulator layer to the first surface with the at least one capacitor registration feature and the at least one ceramic insulator layer registration feature in substantial alignment; and
attaching the ceramic insulator layer to the first surface, wherein attaching the ceramic insulator layer to the first surface comprises laminating the ceramic insulator layer to the capacitor at a temperature between about 800° C. and about 900° C. and a pressure of between about 800 psi and about 1500 psi.

2. The method of claim 1, wherein the at least one ceramic insulator layer registration feature comprises at least one registration aperture, wherein the at least one capacitor registration feature comprises at least one capacitor registration aperture, wherein the method further includes placing a registration pin in the at least one capacitor registration aperture, and wherein contacting the ceramic insulator layer to the first surface with the at least one capacitor registration feature and the at least one ceramic insulator layer registration feature in substantial alignment comprises contacting the ceramic insulator layer to the first surface and placing the at least one registration aperture of the ceramic insulator layer about the at least one registration pin.

3. The method of claim 1, wherein the at least one ceramic insulator layer registration feature comprises at least one registration aperture, wherein the at least one capacitor registration feature comprises at least one registration protrusion, and wherein contacting the ceramic insulator layer to the first surface with the at least one capacitor registration feature and the at least one ceramic insulator layer registration feature in substantial alignment comprises contacting the ceramic insulator layer to the first surface and placing the at least one registration aperture of the ceramic insulator layer about the at least one registration protrusion.

4. The method of claim 1, wherein the at least one ceramic insulator layer registration feature comprises a ceramic insulator layer perimeter, wherein the at least one capacitor registration feature comprises at least one registration protrusion along a perimeter of the capacitor, and wherein contacting the ceramic insulator layer to the first surface with the at least one capacitor registration feature and the at least one ceramic insulator layer registration feature in substantial alignment comprises contacting the ceramic insulator layer to the first surface and engaging the ceramic insulator layer perimeter with the at least one registration protrusion.

5. The method of claim 1, further comprising cutting at least one feedthrough aperture in the ceramic insulator layer prior to substantially aligning the at least one capacitor registration feature formed on the first surface of the capacitor with the at least one ceramic insulator layer registration feature formed in the ceramic insulator layer.

6. The method of claim 1, further comprising cutting at least one feedthrough aperture in the ceramic insulator layer prior to laminating the ceramic insulator layer to the first surface.

7. The method of claim 1, further comprising cutting at least one feedthrough aperture in the ceramic insulator layer after to laminating the ceramic insulator layer to the first surface.

8. A method comprising:
substantially aligning at least one capacitor registration feature formed on a first surface of a capacitor with at least one ceramic insulator layer registration feature formed in a ceramic insulator layer;

contacting the ceramic insulator layer to the first surface with the at least one capacitor registration feature and the at least one ceramic insulator layer registration feature in substantial alignment;

attaching the ceramic insulator layer to the first surface; and cutting at least one feedthrough aperture in the ceramic insulator layer after to laminating the ceramic insulator layer to the first surface.

* * * * *

UNITED STATES PATENT AND TRADEMARK OFFICE
CERTIFICATE OF CORRECTION

| | | |
|---|---|---|
| PATENT NO. | : 8,644,002 B2 | Page 1 of 1 |
| APPLICATION NO. | : 13/149600 | |
| DATED | : February 4, 2014 | |
| INVENTOR(S) | : Rajesh V. Iyer | |

It is certified that error appears in the above-identified patent and that said Letters Patent is hereby corrected as shown below:

In the Claims

Col. 16, line 61, delete "layer after to laminating the ceramic" and insert in place thereof -- layer after laminating the ceramic --;

Col. 17, line 8, delete "layer after to laminating the ceramic" and insert in place thereof -- layer after laminating the ceramic --.

Signed and Sealed this
Seventh Day of October, 2014

Michelle K. Lee
*Deputy Director of the United States Patent and Trademark Office*